United States Patent [19]

Dervaes et al.

[11] Patent Number: 5,393,402
[45] Date of Patent: Feb. 28, 1995

[54] ELECTRODE WITH CRYSTAL MEMBRANE

[75] Inventors: Nelson E. Dervaes; John R. Dunkle, both of Loveland, Colo.

[73] Assignee: Hach Company, Loveland, Colo.

[21] Appl. No.: 145,765

[22] Filed: Feb. 9, 1994

[51] Int. Cl.$^6$ .......................... G01N 27/26; B32B 3/26
[52] U.S. Cl. ................................... 204/419; 204/416; 204/153.13; 264/135
[58] Field of Search ................... 204/416, 419, 153.13, 204/282, 435; 264/135, 299

[56] References Cited

U.S. PATENT DOCUMENTS 3,442,782  5/1969  Shiller et al. .................... 204/419
4,021,325  5/1977  Pungor et al. ................... 204/419

Primary Examiner—John Niebling
Assistant Examiner—Bruce F. Bell
Attorney, Agent, or Firm—Dean P. Edmundson

[57] ABSTRACT

An improved electrode is described having a replaceable cap in which a crystal membrane is mechanically secured. Leakage around the crystal membrane is avoided. The cap can be easily and quickly replaced, as desired.

8 Claims, 4 Drawing Sheets

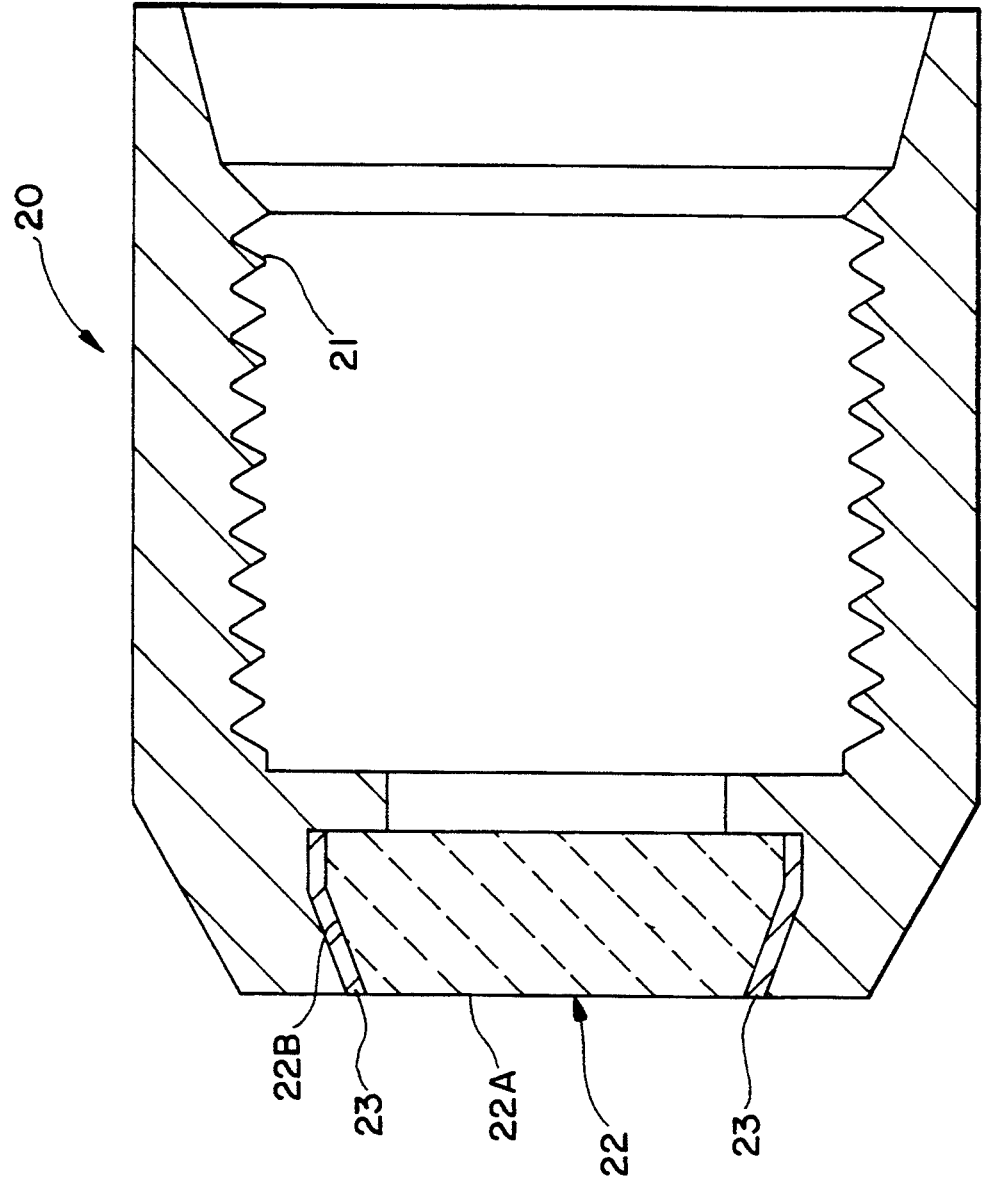

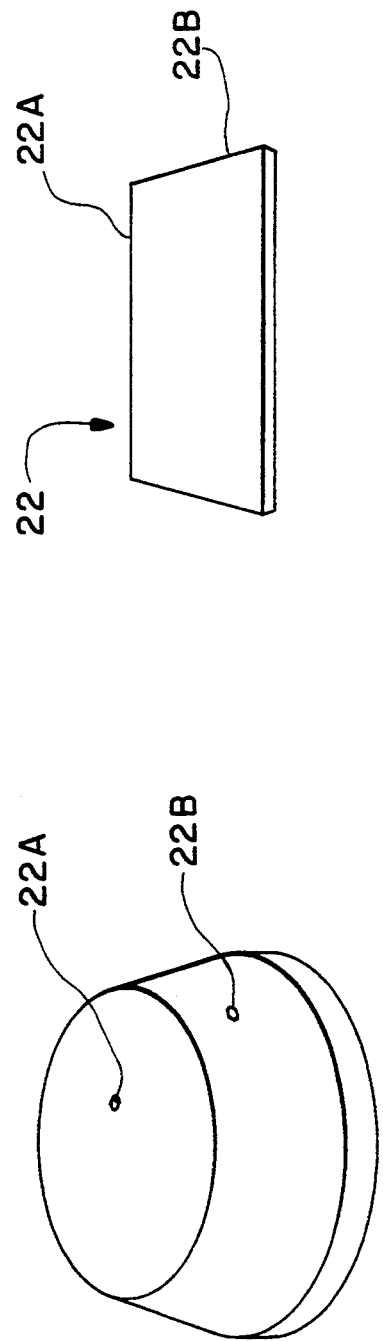

5,393,402

ELECTRODE WITH CRYSTAL MEMBRANE

FIELD OF THE INVENTION

This invention relates to ion-selective electrodes, e.g., electrodes useful for detecting fluoride ion in a liquid sample. More particularly, this invention relates to methods and techniques for retaining and sealing a crystal membrane in the electrode.

BACKGROUND OF THE INVENTION

Electrodes which are used to detect and measure the amount of fluoride ion in a liquid medium (e.g., water) utilize a crystal membrane retained in one end of an elongated barrel. The electrode comprises a crystal membrane, a housing, an internal filling solution, a silver chloride wire, a cap, and a cable terminating normally with a BNC connector.

The fluoride electrode, connected with a reference electrode and placed in a liquid sample, generates a voltage signal which is proportional to the fluoride concentration in the sample. The crystal membrane in the probe is in contact with the internal filling solution and an external sample solution.

The filling solution contains set concentrations of chloride and fluoride ions. The chloride ions establish a voltage with the internal silver/silver chloride reference element and the fluoride ions establish an equilibrium and potential across the membrane. This potential varies only with the fluoride ion concentration (activity) in the sample.

The reference electrode, which is required to complete the electrical circuit through a pH/mV meter, establishes a stable, reproducible potential. In the completed cell, only the potential across the crystal membrane varies.

The crystal membrane preferably comprises lanthanum fluoride doped with europium fluoride (e.g., 0.3%). Alternatively, the crystal membrane may comprise cerium fluoride doped with europium fluoride. The size of the membrane may vary. Preferably the exposed surface of the membrane is flat and polished.

In the conventional electrode, the cylindrical crystal membrane is secured in a cylindrical plastic cup by means of a potting compound (bonding agent) which is very expensive. The process of securing the crystal is time-consuming, expensive and unreliable. The plastic cup must then be bonded into an elongated plastic housing. The presence of any gaps or delamination between the crystal membrane and the potting compound (either during manufacture or after the electrode has been used) allows the internal filling solution in the electrode to contact the sample solution, thereby creating a current path around the crystal and rendering the electrode inaccurate. More critical delamination creates a short circuit, rendering the electrode useless. Eventually the crystal can fall out of the electrode.

There has not heretofore been provided a method or technique for effectively and easily securing the crystal in the electrode.

SUMMARY OF THE INVENTION

In accordance with the present invention there is provided an improved technique for effectively securing the crystal membrane to a support for use in an electrode. The improved technique provides an electrode which is less expensive to produce than has been previously possible. The improved electrode is also more reliable than prior electrodes and is less likely to fail.

In one embodiment the improved technique comprises:

(a) providing a crystal membrane which has an outwardly projecting peripheral surface;
(b) applying a sealant to the peripheral surface;
(c) molding a plastic support means around said peripheral surface of the crystal membrane.

The support means may comprise, for example, a cap member which includes a threaded end. This type of support can be threaded onto one end of an elongated barrel to form an electrode useful for detecting fluoride in a liquid medium.

The crystal membrane has a shape which enables it to be mechanically locked to the plastic support means. For example, the crystal membrane may have the shape of a truncated cone, or it may include flanges, or tabs, or recesses, etc. so that it becomes mechanically locked to the plastic which is molded around the edges of the crystal membrane.

Other advantages of the process and electrode of the invention will be apparent from the following detailed description.

BRIEF DESCRIPTION OF THE DRAWINGS

The invention is described in more detail hereinafter with reference to the accompanying drawings, wherein like reference characters refer to the same parts throughout the several views and in which:

FIG. 1 is a cross-sectional view showing a molded cap member produced in accordance with the techniques of this invention, with the crystal membrane firmly secured in one end of the cap member;

FIG. 2 is a perspective view of one embodiment of crystal membrane which may be used in the practice of this invention;

FIG. 3 is a side elevational view of the membrane of FIG. 2;

DETAILED DESCRIPTION OF THE INVENTION

Figure 4:
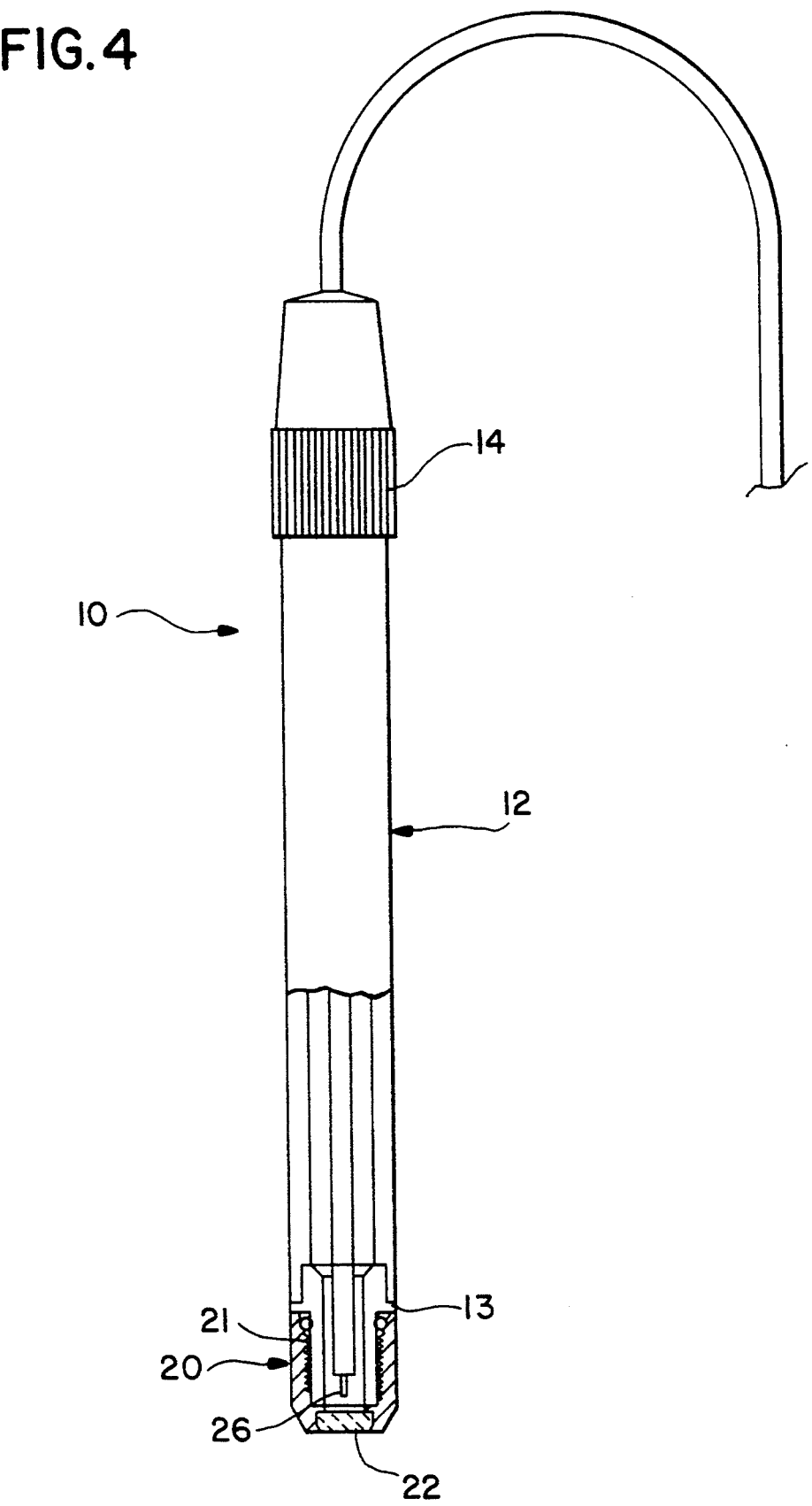
FIG. 4 is a cross-sectional view of an electrode produced in accordance with this invention.

In the drawings there is shown an improved electrode 10 produced in accordance with this invention. The electrode comprises an elongated tubular barrel 12 having a lower end 13 and an upper end 14. Threadably secured to the lower end of the barrel is a cap member 20 (also shown in FIG. 1) in which a crystal membrane 22 is secured. The internal cavity of the barrel is filled with an internal filling solution. A wire 26 is immersed in the internal filling solution in the barrel and extends out through the upper end of the barrel and terminates at a connector such as a BNC connector.

The cap member 20 includes a (first end) threaded end 21 which enables it to be easily attached to the lower end of the barrel of the electrode. This arrangement conveniently enables one cap member to be removed and replaced with another cap member whenever necessary, without having to change the entire electrode.

The crystal membrane around which the cap member 20 is molded in situ preferably comprises lanthanum fluoride (doped with 0.3% europium fluoride). The thickness of the membrane may vary, although typically a thickness in the range of about 1.5 to 3 mm. is sufficient. The lower end of cap member 20 in which the crystal membrane is secured may be referred to as the second end.

Although it is not necessary for the crystal membrane to have a flat or planar exposed surface, this is preferred. The membrane may be disk-shaped, square, triangular, oval, etc. It may include outwardly-extending tabs, flanges or legs, or it may be a truncated cone or disk as shown in the drawings.

The preferred shape for the crystal is a truncated cone, as illustrated in the drawings, having a flat or planar surface 22A and an outwardly-sloping surface 22B. A thin layer of conventional sealant (e.g., silicone RTV) is preferably applied to the sloping surface 22B and the perimeter of the crystal prior to molding the plastic cap around the crystal. Preferably the sealant completely coats the crystal periphery. The presence of the sealant facilitates good sealing between the surfaces of the crystal and the plastic. Other types of chemically-resistant flexible sealants could also be used. A solid gasket, such as an O-ring, could be used instead of a chemical sealant and is considered to be equivalent to a chemical sealant for use herein.

The plastic which is heated and molded around the perimeter of the crystal is preferably polyester, but any conventional thermoplastic material may be used for this purpose. The plastic should have a moderate rate of shrink to ensure sufficient compression on the sealant when the plastic cools. It should also be highly chemically resistant. Preferred plastics should be flexible but not soft or brittle. The crystal membrane is supported in an appropriately-shaped mold and then the plastic (heated to a temperature of about 250° C.) is injected into the mold so that the plastic flows around the perimeter of the crystal membrane and over the outwardly-projecting sloped surface of the crystal membrane. If desired, the crystal membrane may be pre-heated before the plastic is injected. Some of the plastic is also permitted to flow over a portion of the bottom surface 22C of the crystal membrane. After the plastic cools and hardens, the completed cap 20 can be removed from the mold. The crystal membrane is mechanically locked to the cap by means of the plastic extending over the sloped surface and along a portion of the bottom surface of the crystal membrane.

Figure 5:
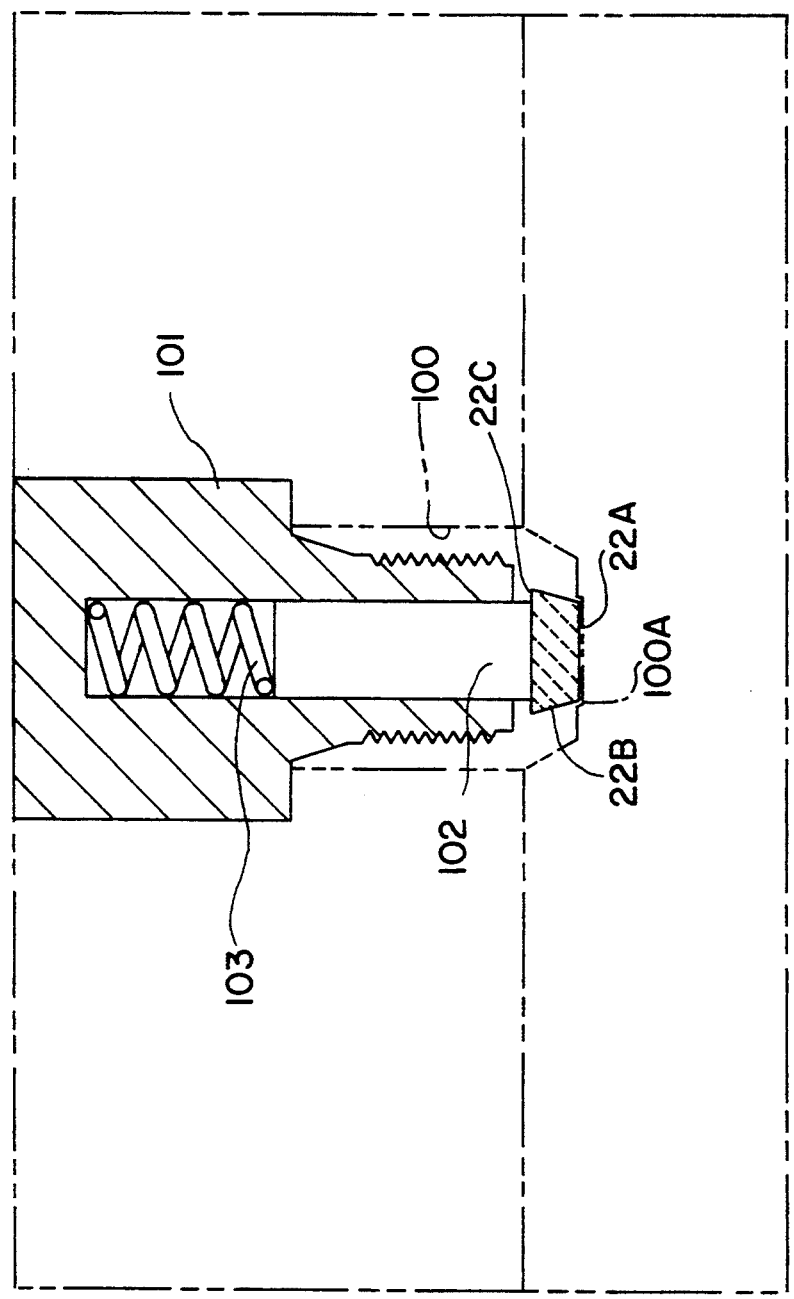
FIG. 5 is an elevational, partially cut-away view showing one manner in which a crystal membrane may be supported in a mold during formation of a plastic cap around the membrane.

FIG. 5 is a side elevational view illustrating the positioning of the crystal membrane 22 in a mold cavity 100. The perimeter of the crystal membrane is coated with a sealant 23 and allowed to cure prior to placing the membrane face down in pocket or depression 100A in the mold. The mold is then closed, after which the core 101 is threaded into the mold to the position shown. An inner core 102 is urged against the backside of the membrane by means of spring 103, as shown, in order to hold the crystal membrane in place. The core has a diameter smaller than the diameter of the membrane, as shown, so that the molten plastic can flow along a portion of the rear face of the membrane. Then the molten plastic is injected into the mold. After the molding has been completed the core is removed and the molded cap with membrane secured therein can be removed. The plastic extending over the face 22A of the membrane is then ground away, after which the surface of the membrane is polished.

Other variants are possible without departing from the scope of this invention.

What is claimed is:

1. An electrode cap member comprising a tubular body having first and second ends and a crystal membrane permanently secured therein; wherein said first end is threaded, and wherein said crystal membrane is secured in said second end; wherein said crystal membrane includes a surface which is exposed to the exterior of said cap member and also includes a rear surface; and wherein said cap member includes a portion which extends over said rear surface of said crystal membrane such that said crystal membrane is permanently secured in said cap member.

2. An electrode cap member in accordance with claim 1, wherein said crystal membrane comprises a truncated cone.

3. An electrode cap member in accordance with claim 1, further comprising a sealant between said crystal membrane and said body.

4. An electrode cap member in accordance with claim 1, wherein said crystal membrane comprises lanthanum fluoride.

5. An electrode cap member in accordance with claim 4, wherein said lanthanum fluoride has been doped with 0.3% europium fluoride.

6. In combination with an electrode body of the type having an elongated barrel with a lower end which is threaded, a cap member having first and second ends; wherein said first end threadably engages said lower end of said barrel; wherein said cap member includes a crystal membrane permanently secured in said second end; wherein said crystal membrane includes a rear surface; and wherein said cap member includes a portion which extends over said rear surface of said crystal membrane such that said crystal membrane is permanently secured in said cap member.

7. A combination in accordance with claim 6, wherein said crystal membrane comprises a truncated cone.

8. A method for securing a crystal membrane in one end of a cap member, the method comprising:
   (a) providing said crystal membrane with a shape which includes a face portion, a rear surface and an outwardly projecting portion;
   (b) molding plastic around said crystal membrane in a manner such that plastic covers said outwardly projecting portion of said crystal membrane and a portion of said rear surface.

* * * * *